United States Patent [19]

Irvine

[11] Patent Number: Plant 6,898

[45] Date of Patent: Jul. 4, 1989

[54] RHODODENDRON PLANT—IRVSMART VARIETY

[76] Inventor: Ray Irvine, 1211 Bell Rd., Apt. 55, Antioch, Tenn. 37013

[21] Appl. No.: 184,248

[22] Filed: Apr. 19, 1988

[51] Int. Cl.[4] ..... A01H 5/00
[52] U.S. Cl. ..... Plt./56
[58] Field of Search ..... Plt./55–56

*Primary Examiner*—Robert E. Bagwill

*Attorney, Agent, or Firm*—Burns, Doane, Swecker & Mathis

[57] ABSTRACT

A new and distinct variety of Rhododendron plant which originated as a sporting branch on the P.J.M. variety is provided. Unlike the parent the new variety exhibits dwarf and compact plant characteristics. The attractive red-purple blooms are identical in coloration to those of the parent; however, the blooms are smaller than those of the parent as are other elements of the plant. Blooming commonly takes place in U.S.D.A. Zone 7 during the second half of April.

1 Drawing Sheet

SUMMARY OF THE INVENTION

The new variety Rhododendron plant was discovered by me during 1982 as a sporting branch which appeared on one of many plants of the P.J.M. variety (non-parented) growing under cultivation on my farm at Smithville, Tenn. The P.J.M. parent variety was known to be a hybrid of *Rhododendron dauricum sempervirens*×*Rhododendron carolinianum.*

I was attracted to the new variety by the distinctive appearance of the sporting branch which exhibited an unusual dwarf appearance. Cuttings from the sporting branch were taken and rooted to form additional plants of the new variety. These were grown to form mature plants which have been carefully observed.

It was found that the following combination of characteristics is exhibited by the new variety of Rhododendron plant:

(a) exhibits a dwarf and compact growth habit unlike that of the P.J.M. variety,
(b) forms blossoms which are smaller than those of the P.J.M. variety and which are of a red-purple coloration substantially identical to that of the P.J.M. variety, and
(c) possesses leaf and stem colorations which are substantially identical to those of the P.J.M. variety.

The plant parts of the new variety are smaller than those of the P.J.M. variety and tend to be correspondingly proportional in size to those of the parent variety. The branching characteristics also are similar to those of the parent variety, but are present on a dwarf plant.

The new variety has been successfully propagated through the traditional means of cuttage as well as through the in vitro culture. Such asexual propagation has demonstrated that the unique combination of characteristics has been well established and is transmitted to successive generations.

The new variety has been named the Irvsmart variety.

BRIEF DESCRIPTION OF THE PHOTOGRAPHS

The accompanying photographs show typical specimens of the new variety of Rhododendron plant as depicted in color as true as is reasonably possible to make the same in color illustrations of this character.

The plant growth habit, size, scale of foliage and blossoms are illustrated. The specimens illustrated were grown in a soilless medium at Nashville, Tenn.

DETAILED DESCRIPTION

Figure 1:
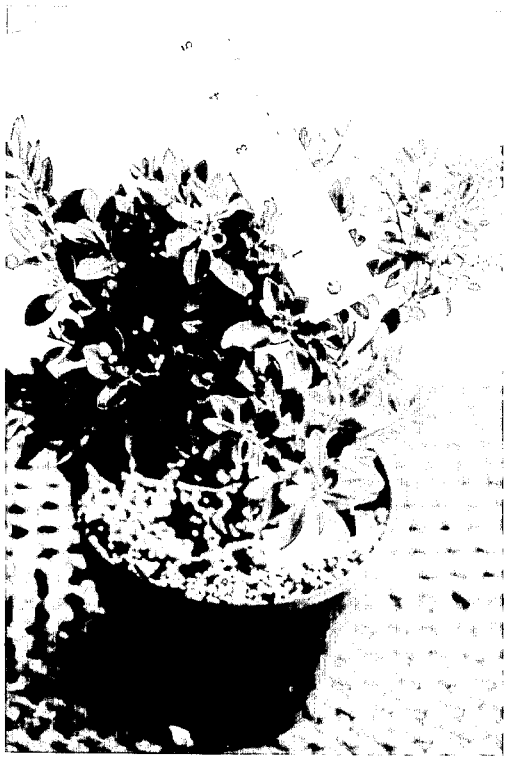
FIG. 1 illustrates a specimen of a typical 1½ year old plant of the new variety growing on its own roots wherein the compact growth habit is apparent.
Figure 2:
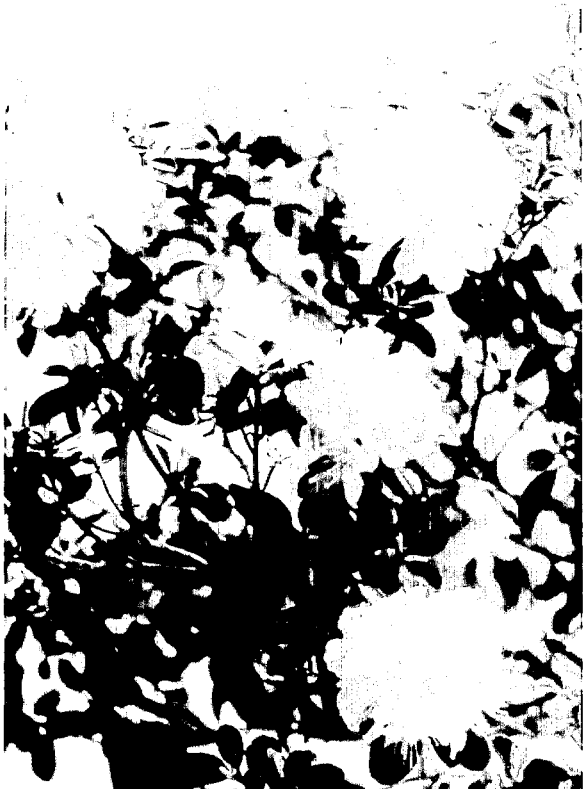
FIG. 2 illustrates typical blossoms and foliage of a more mature plant of the new variety during late April wherein the attractive red-purple blossom coloration is apparent.

The following is a detailed description of the new Rhododendron variety with color terminology in accordance with the R.H.S. Colour Chart of The Royal Horticultural Society, London, England. The description was prepared following the observation of representative plants grown at West Grove, Pa.

Type: Broadleaf evergreen flowering shrub of the Rhododendron genus.

Plant habit: Somewhat rounded at maturity and slightly taller than broad. Untrimmed plants growing in the landscape are projected to assume a height of approximately one-half that of the parent P.J.M. variety at ages of 5 and 10 years.

Foliage:

*Shape.*—Elliptic with an acute apex and obtuse base.

*Size.*—Approximately 2.2 to 3.0 cm. in length on average, and approximately 1.2 to 1.6 cm. in width on average. The foliage of the parent P.J.M. variety commonly exhibits a length of approximately 3.5 to 5.0 cm. on average and a width of approximately 1.7 to 2.3 cm. on average.

*Color.*—The summer foliage commonly corresponds to Yellow-Green Group 147A and is substantially identical in coloration to that of the parent variety. The winter foliage commonly is deep purplish bronze with deep green undertones and is substantially identical in coloration to that of the parent variety. Such coloration commonly is between Greyed-Purple Group 187B and Greyed-Purple Group 187B.

Stems:

*Color.*—Reddish green in summer and purplish red with green undertones in the winter. Such coloration is substantially identical to that of the parent variety.

*Growth.*—A flush of new growth commonly averages approximately $1\frac{1}{2}$ to $2\frac{1}{2}$ inches in length which is commonly one-third to one-half the length commonly exhibited by the parent variety.

Flowers:

*Size.*—Approximately 4.5 to 5.5 cm. on average.

*Color.*—The fully open blooms commonly are between Red-Purple Group 73A and 75A and are substantially identical in coloration to that of the parent variety.

Blooming period: The blossoming commonly takes place in U.S.D.A. Zone 7 during the second half of April. Such blooming period commonly is identical to that of the parent variety.

I claim:

1. A new and distinct variety of Rhododendron plant, characterized particularly as to novelty by the following combination of characteristics:

(a) exhibits a dwarf and compact growth habit unlike that of the P.J.M. variety, (b) forms blossoms which are smaller than those of the parent P.J.M. variety and which are of a red-purple coloration substantially identical to that of the P.J.M. variety, and (c) possesses leaf and stem colorations which are substantially identical to those of the P.J.M. variety, substantially as illustrated and described together with the parts thereof.

* * * * *